US007761144B2

(12) United States Patent
Cox et al.

(10) Patent No.: US 7,761,144 B2
(45) Date of Patent: Jul. 20, 2010

(54) METHOD, APPARATUS, AND COMPUTER PROGRAM PRODUCT FOR STOCHASTIC PSYCHO-PHYSIOLOGICAL ASSESSMENT OF ATTENTIONAL IMPAIRMENTS

(75) Inventors: Daniel J. Cox, Charlottesville, VA (US); Boris P. Kovatchev, Charlottesville, VA (US); Rayna S. Robeva, Charlottesville, VA (US); Jennifer Kim Penberthy, Manakin Sabot, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 258 days.

(21) Appl. No.: 10/592,883

(22) PCT Filed: Mar. 17, 2005

(86) PCT No.: PCT/US2005/008908

§ 371 (c)(1),
(2), (4) Date: Sep. 15, 2006

(87) PCT Pub. No.: WO2005/089431

PCT Pub. Date: Sep. 29, 2005

(65) Prior Publication Data

US 2008/0220400 A1    Sep. 11, 2008

Related U.S. Application Data

(60) Provisional application No. 60/554,113, filed on Mar. 18, 2004.

(51) Int. Cl.
*A61B 5/04* (2006.01)
*A61B 5/00* (2006.01)
*A61B 19/00* (2006.01)

(52) U.S. Cl. ............... 600/544; 600/300; 128/920; 128/898

(58) Field of Classification Search ............... 600/544, 600/545, 300, 481, 483; 128/920–925
See application file for complete search history.

(56) References Cited

U.S. PATENT DOCUMENTS 4,407,299 A * 10/1983 Culver ................. 600/544

(Continued)

OTHER PUBLICATIONS

Amen, D.G, et al., "High-Resolution Brain SPECT Imaging in ADHD," Annals of Clinical Psychiatry, vol. 9, No. 2, pp. 81-86, (1997).

(Continued)

*Primary Examiner*—Charles A Marmor, II
*Assistant Examiner*—Navin Natnithithadha
(74) *Attorney, Agent, or Firm*—Novak Druce DeLuca + Quigg LLP; Robert J. Decker

(57) ABSTRACT

A method, apparatus, and computer program product that provides, among other things, a procedure for the enhanced assessment of attention-related impairments of individuals. Further, the method, apparatus, and computer program product enhances existing assessment instruments by providing a way to reduce diagnostic error through the combining of the results of disparate assessment instruments. Potential users of this product will be any person or organization that diagnoses or treats persons with attentional or cognitive impairments. The method can be used for initial screening and diagnosis of disorders associated with impaired attention, such as ADHD, as well as for treatment and evaluation of the effects of treatments, such as medication or additional therapies.

30 Claims, 5 Drawing Sheets

U.S. PATENT DOCUMENTS

| | | | |
|---|---|---|---|
| 4,408,616 A * | 10/1983 | Duffy et al. | 600/544 |
| 4,421,122 A | 12/1983 | Duffy | |
| 4,846,190 A | 7/1989 | John | |
| 4,862,359 A * | 8/1989 | Trivedi et al. | 600/544 |
| 4,913,160 A | 4/1990 | John | |
| 5,083,571 A | 1/1992 | Prichep | |
| RE34,015 E * | 8/1992 | Duffy | 600/544 |
| 5,176,145 A | 1/1993 | Ryback et al. | |
| 5,287,859 A | 2/1994 | John | |
| 5,309,923 A | 5/1994 | Leuchter et al. | |
| 5,310,195 A | 5/1994 | Abdallah | |
| 5,377,100 A | 12/1994 | Pope | |
| 5,406,957 A | 4/1995 | Tansey | |
| 5,447,166 A * | 9/1995 | Gevins | 600/544 |
| 5,549,118 A | 8/1996 | John | |
| 5,550,021 A | 8/1996 | Blum et al. | |
| 5,676,138 A * | 10/1997 | Zawilinski | 600/301 |
| 5,724,987 A | 3/1998 | Gevins et al. | |
| 5,913,310 A | 6/1999 | Brown | |
| 5,983,129 A | 11/1999 | Cowan et al. | |
| 6,044,292 A | 3/2000 | Heyrend et al. | |
| 6,097,980 A | 8/2000 | Monastra et al. | |
| 6,115,631 A | 9/2000 | Heyrend et al. | |
| 6,132,724 A * | 10/2000 | Blum | 424/725 |
| 6,186,145 B1 | 2/2001 | Brown et al. | |
| 6,210,950 B1 | 4/2001 | Johnson et al. | |
| 6,366,813 B1 | 4/2002 | DiLorenzo | |
| 6,434,419 B1 * | 8/2002 | Gevins et al. | 600/544 |
| 6,496,724 B1 * | 12/2002 | Levendowski et al. | 600/544 |
| 6,622,036 B1 * | 9/2003 | Suffin | 600/544 |
| 6,625,485 B2 * | 9/2003 | Levendowski et al. | 600/544 |
| 6,746,409 B2 | 6/2004 | Keirsbilck | |
| 6,843,774 B2 | 1/2005 | Foust et al. | |
| 6,947,790 B2 * | 9/2005 | Gevins et al. | 600/544 |
| 7,177,675 B2 * | 2/2007 | Suffin et al. | 600/544 |
| 7,347,818 B2 * | 3/2008 | Simon | 600/300 |
| 7,489,964 B2 * | 2/2009 | Suffin et al. | 600/544 |
| 2002/0183644 A1 * | 12/2002 | Levendowski et al. | 600/544 |
| 2003/0013981 A1 * | 1/2003 | Gevins et al. | 600/544 |
| 2003/0065535 A1 | 4/2003 | Karlov | |
| 2003/0135128 A1 * | 7/2003 | Suffin et al. | 600/544 |
| 2004/0059241 A1 * | 3/2004 | Suffin | 600/544 |
| 2004/0138582 A1 * | 7/2004 | Connolly et al. | 600/544 |
| 2004/0193068 A1 * | 9/2004 | Burton et al. | 600/544 |

OTHER PUBLICATIONS

Biederman, J., et al., "Motor preference, major depression and psychosocial dysfunction among children with attention deficit hyperactivity disorder," J. of Psychiatric Research, vol. 28, No. 2, pp. 171-184, (1994).

Cox, D. J., et al., "Electroencephalographic and Psychometric Differences Between Boys With and Without Attention-Deficit/Hyperactivity Disorder (ADHD): A Pilot Study," Applied Psychophysiology and Biofeedback, vol. 23, No. 3, pp. 179-188., (1999).

Crawford, H., et al., "Quantitative EEG magnitudes in children with and without attention deficit disorder during neurological screening and cognitive tasks," Child Study Journal, vol. 26, No. 1, pp. 71-86, (1996).

Goyette, C. H., "Normative Data on Revised Conners Parent and Teacher Rating Scales," J. of Abnormal Child Psychology, vol. 6, No. 2, pp. 221-236, (1978).

Merkel, R. L., et al., "The EEG Consistency Index as a Measure of Attention Deficit/Hyperactivity Disorder and Responsiveness to Medication: A Double blind Placebo Controlled Pilot study," Applied Psychophysiology and Biofeedback vol. 25, No. 3 pp. 133-142, (2000).

Schachar, R., et al., "Deficient inhibitory control in Attention Deficit Hyperactivity Disorder," J. of Abnormal Child Psychology, vol. 23, No. 4, pp. 411-437, (1995).

Tannock, R., et al., "Methylphenidate and cognitive flexibility: Dissociated dose effects in hyperactive children," J. of Abnormal Child Psychology, vol. 23, No. 2, pp. 235-266, (1995).

Vaidya, C. J., et al., "Selective effects of methylphenidate in attention deficit hyperactivity disorder: A functional mangetic resonance study," Proc. Natl. Acad. Sci. USA, vol. 95, 14494-14499, (1998).

Chabot, R. J., et al., "Quantitative Electroencephalographic Profiles of Children with Attention Deficit Disorder," Society of Biological Psychiatry, vol. 40, pp. 951-963, (1996).

Monastra, V. J., "Assessing Attention Deficit Hyperactivity Disorder via Quantitative Electroencephalography: An Initial Validation Study," Neuropsychology, vol. 13, No. 3, pp. 424-433, (1999).

Ritchie, K., et al., "Classification criteria for mild cognitive impairment: A population-based validation study," Neurology, vol. 56, No. 1, pp. 37-42, (2001).

Ballard, C., et al., "Attention and Fluctuating Attention in Patients with Dementia with Lewy Bodies and Alzheimer Disease," Archives of Neurology, vol. 58, No. 6, pp. 977-982, (2001).

Grodstein, F., et al., "Type 2 Diabetes and Cognitive Function in Community-Dwelling Elderly Women," Diabetes Care, vol. 24, No. 6, pp. 1060-1065, (2001).

Sohlberg, M., et al., "Improving Attention and Managing Attentional Problems: Adapting Rehabilitation Techniques to Adults with ADD," Annals of New York Academy of Sciences, vol. 931, pp. 359-375, (2001).

Armstrong, C., et al., "Neurocognitive Problems in Attention Deficit Disorder: Alternative Concepts and Evidence for Impairment in Inhibition of Selective Attention," Annals of New York Academy of Sciences, vol. 931, pp. 196-215, (2001).

Meyer, J., et al., "Cardiovascular and Other Risk Factors for Alzheimer's Disease and Vascular Dementia," Annals of New York Academy of Sciences, vol. 903, pp. 411-423, (2000).

Chang, L., et al., "Neural correlates of attention and working memory deficits in HIV patients," Neurology, vol. 57, No. 6, pp. 1001-1007, (2001).

Pohjasvaara, T., et al., "Evaluation of Various Methods of Assessing Symptoms of Cognitive Impairment and Dementia," Alzheimer Disease and Associated Disorders, vol. 15, No. 4, pp. 184-193, (2001).

Doraiswamy, P. M., et al., "The Alzeheimer's Disease Assessment Scale: Evaluation fo Psychometric Properties and Patterns of Cognitive Decline in Multicenter Clinical Trials of Mild to Moderate Alzheimer's Disease," Alzheimer Disease and Associated Disorders, vol. 15 No. 4, pp. 174-183, (2001).

Goldman, L.S., et al., "Council Report of Diagnosis and Treatment of ttention-Deficit/ Hyperactivity Disorder in Children and Adolescents," J. of the American Medical Association, vol. 279, pp. 1100-1107, (1998).

Clarke, A. R., et al., "EEG analysis in attention-deficit/hyperactivity disorder: A comparative study of two subtypes," Psychiatry Research, vol. 81, pp. 19-29, (1998).

McDonald, S., "Covert orienting and focusing of attentioin in children with attention deficit hyperactivity disorder," Neuropsychologia, vol. 37, No. 3, pp. 345-356, (1999).

Kovatchev, B.P., "A Psychophysiological Marker of Attention Deficit/Hyperactivity Disorder (ADHD) Defining the EEG Consistency Index," Applied Psychophysiology and Biofeedback, vol. 26, No. 2, (2001).

* cited by examiner

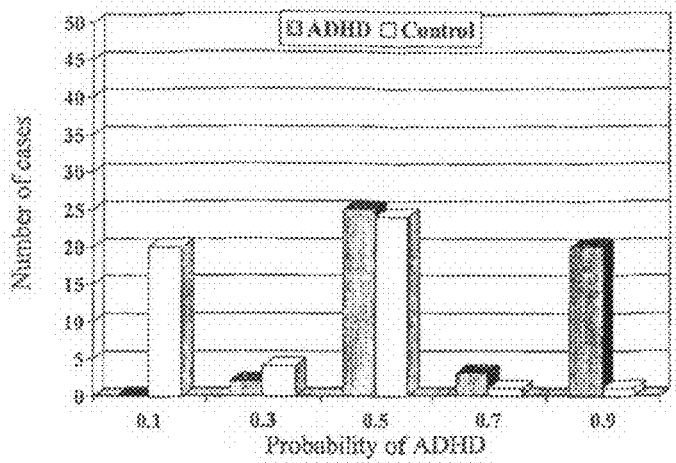
FIG. 5A: Subject Distribution After Test 1
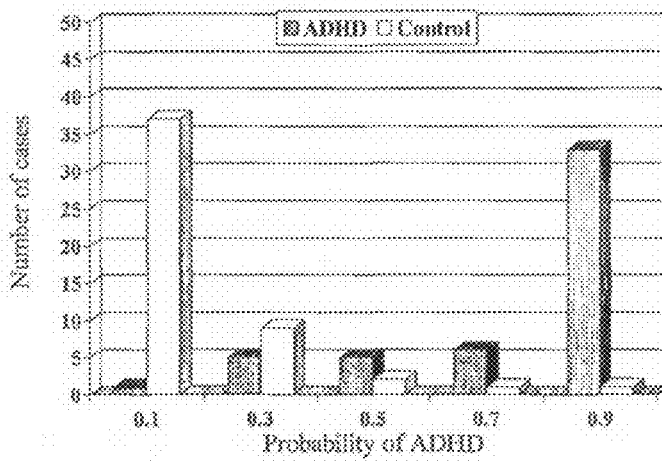
FIG. 5B: Subject Distribution After Tests 1+2
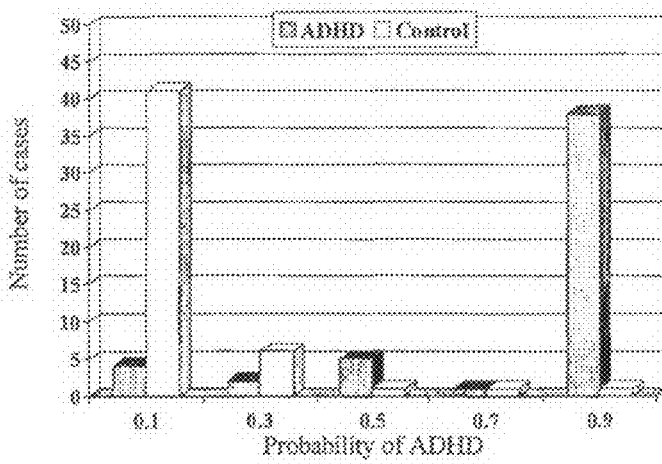
FIG. 5C: Subject Distribution After Tests 1+2+3

METHOD, APPARATUS, AND COMPUTER PROGRAM PRODUCT FOR STOCHASTIC PSYCHO-PHYSIOLOGICAL ASSESSMENT OF ATTENTIONAL IMPAIRMENTS

CROSS-REFERENCES TO RELATED APPLICATIONS

This application is a national stage filing of International Application No. PCT/US2005/008908 filed Mar. 17, 2005, which claims benefit of priority under 35 U.S.C. Section 119(e) from U.S. Provisional Patent Application Ser. No. 60/554,113 filed Mar. 18, 2004, entitled "Method, Apparatus, and Computer Program Product for Stochastic Psychophysiological Assessment of ADHD," the disclosures of which are hereby incorporated by reference herein in their entirety.

The present application is also related to PCT International Application No. PCT/US02/14188, filed May 6, 2002, entitled "Method, Apparatus, and Computer Program Product for Assessment of Attentional Impairments," and corresponding U.S. patent application Ser. No. 10/476,826, filed Nov. 3, 2003, of which are both assigned to the present assignee and are both hereby incorporated by reference herein in their entirety. The present invention may be implemented with the technology discussed throughout the International Application No. PCT/US02/14188 and U.S. application Ser. No. 10/476,826.

FIELD OF THE INVENTION

The present invention relates to the assessment of individuals with attentional impairments, and more particularly the performance of meta-analysis of data obtained using disparate assessment instruments for attentional impairment.

BACKGROUND OF THE INVENTION

Impairments in cognitive ability and attention are pervasive and potentially debilitating components of many disorders, conditions, injuries and diseases, including mild cognitive impairment (MCI) in persons with pre-dementia, dementia, dementia with Lewy bodies, Alzheimer's Disease, traumatic brain injury, Attention Deficit/Hyperactivity Disorder (ADHD), and cognitive/attentional declines associated with chronic diseases such as diabetes, cardiovascular disease, and HIV infection [1, 2, 3, 4, 5, 6, 7, 8]. Most of these disorders are assumed to be pathology-based and therefore amenable to intervention, especially if diagnosed early.

ADHD is one of multiple disorders associated with impairments in attention. Although this document may particularly identify attentional disorders associated with ADHD, the various embodiments of the present invention shall be applied to any disorder with associated attentional impairments. With respect to dementia, recent research and a review of the literature conclude that the frequency of post stroke dementia and cognitive decline varied sharply when different systems of diagnostic classification and methods were used [10]. Furthermore, recent findings support the need for validation not only of the criteria, but also the need for validated measures to diagnosis dementia and cognitive impairment post stroke [10, 11, 12], and Alzheimer's disease [13]. In addition, cognitive abnormalities commonly occur in patients with HIV infection [14]. Among otherwise healthy HIV-positive patients, cognitive deficits are thought to be infrequent [15], but some investigators suggest that more sensitive measures may be needed to detect the mild cognitive decline during the asymptomatic stage [16].

The hallmarks of ADHD are hyperactivity, impulsivity, and an inability to sustain attention. The DSM-IV distinguishes three types: predominantly inattentive type, predominantly hyperactive-impulsive type, and combined type. In addition to the core clinical symptoms of ADHD, high levels of co-morbidity have been found with learning, oppositional defiant, conduct, mood, and anxiety disorders. Furthermore, it is estimated that the majority of children diagnosed with ADHD exhibit significant behavioral problems during adolescence and manifest continuing functional deficits and psychopathology into adulthood. One real-life consequence of ADHD is a five-fold increase in automobile crashes [21].

Early diagnosis and treatment of Alzheimer's disease, dementia, and additional progressive disorders associated with attentional impairment is especially important because patients with early stages of dementia may show reversal of their cognitive deficits and neurochemistry abnormalities after treatment [8].

There are numerous disorders and diseases associated with impairment of attention and cognitive functioning, however, the diagnosis and quantification of impairment of attention in any disease or disorder is typically difficult. Some examples include: attentional impairments associated with ADHD, HIV infection, Alzheimer's Disease, cardiovascular disease, diabetes, and dementia.

With respect to ADHD, the DSM-IV [17] states "The essential features of ADHD are a persistent pattern of inattention and/or hyperactivity-impulsivity that is more frequent and severe than is typically observed in individuals in a comparable level of development." Evidence of six of nine inattentive behaviors and/or six of nine hyperactive-impulsive behaviors must have been present before age seven, and must clearly interfere with social, academic and/or occupational functioning. Consequently, the diagnosis of ADHD is highly dependent on a retrospective report of a patient's past behavior and subjective judgments on degree of relative impairment. Due to the subjective nature of assessment, precision in diagnosis has been elusive. ADHD is complex and influences all aspects of a person's life. It can co-exist with and/or mimic a variety of health, emotional, learning, cognitive, and language problems. An appropriate, comprehensive evaluation for ADHD includes a medical, educational, and behavioral history, evidence of normal vision and hearing, recognition of systemic illness, and a developmental survey. The diagnosis of ADHD should never be made based exclusively on rating scales, questionnaires, or tests [18].

Diagnosing ADHD presents a challenge to traditional assessment paradigms because there is no single assessment tool or medical test that definitively establishes its presence (See Hinshaw, S. P. (1994), "Attention Deficits and Hyperactivity in Children," Thousand Oaks, Calif., Sage, and Penberthy, J. K., Cox, Breton, M., Robeva, R., Kalbfleisch, M. L., Loboschefski T., Kovatchev, B. (2005), "Calibration of ADHD Assessments Across Studies: A Meta-Analysis Tool," Applied Psychophysiology and Biofeedback, Vol. 30, No. 1, pp 31-51, of which are hereby incorporated by reference herein in their entirety). Instead, there are multiple tests of varying design, each of which has its own administration, scoring system, and diagnostic criteria. Unfortunately, none of these individual assessments has proven to be 100 percent accurate in diagnosing ADHD. This is to be expected, however, since ADHD is considered to be a physiologically-based disorder with a multi-factorial etiology that includes neurobiology as an important factor, and would not be easily classified by only one assessment tool. In fact, the reliability of the ADHD diagnosis based on one method or test alone is quite low, and lower still when chance agreement is considered. For example, previous research has found 78 percent agreement between a structured interview and a discharge diagnosis of ADHD (See Welner, Z., Reich, W., Herjanic, B., Jung, K. G. (1987), "Reliability, Validity, and Parent-child Agreement Studies of the Diagnostic Interview for Children and Adolescents (DICA)," Journal of the American Academy of Child and Adolescent Psychiatry, 26(5), 649-653, of which is hereby incorporated by reference herein in it's entirety) and 70 to 80 percent accuracy (with considerable variation depending on age range) of laboratory measures of attention in correctly predicting an ADHD diagnosis (See Fischer, M., Newby, R. F., Gordon, M. (1995), "Who are the False Negatives on Continuous Performance Tests?", Journal of Clinical Child Psychology, 24, 427-433, of which is hereby incorporated by reference herein in it's entirety).

Of even greater importance, there is currently no uniform methodology for calibrating or standardizing the multiple disparate ADHD assessment tools currently available for clinicians and researchers.

What is needed is a methodology for producing a single result from disparate assessments and tests in order to not only provide a more accurate diagnosis, but to also enable the combination of multiple studies of ADHD assessments, thus increasing the sample size and providing more power, generalizability, and possibilities for cross-sectional comparisons. Such a procedure would be especially useful in situations such as diagnosing ADHD, when there is no single conclusive assessment but rather a number of imperfect tests that marginally address the outcome of interest, and where researchers may have multiple related tests performed on a single subject which they wish to combine into a more comprehensive assessment of the individual.

BRIEF SUMMARY OF INVENTION

Various embodiments of the present invention relates to the performance of meta-analysis of data obtained from disparate assessment instruments based on calibration of the data from such instruments into a single scale. This related method and system could be applied to any instance where one wishes to combine data from disparate assessment instruments.

In particular, a first aspect of an embodiment of the present invention is directed to a method, apparatus, and/or computer program product for assessing individuals for disorders associated with attentional impairments. The related method comprises (a) obtaining scores from two or more assessment instruments for attentional impairment, conducted on an individual, (b) calibrating the obtained scores by standardizing the range of obtainable scores for each of the instruments, and (c) operating upon the calibrated scores using a computational procedure to produce a composite result.

Another aspect of an embodiment of the present invention is directed to a method, apparatus and/or computer program product for assessing individuals for disorders associated with attentional impairments, using scores obtained from two or more assessment instruments conducted on an individual. The related apparatus is a device configured to (a) calibrate the obtained scores by standardizing the range of obtainable scores for each of the instruments, and (b) perform a computation procedure upon the calibrated scores to produce a composite result.

These aspects of the various embodiments of the present invention can be integrated together to provide a comprehensive, flexible, and effective diagnostic measure.

These and other objects, along with advantages and features of the invention disclosed herein, will be made more apparent from the description, drawings and claims that follow.

BRIEF SUMMARY OF TEE DRAWINGS

The foregoing and other objects, features, and advantages of the present invention, as well as the invention itself, will be more fully understood from the following description of the invention, when read together with the accompanying drawings, in which.

Figure 3A:
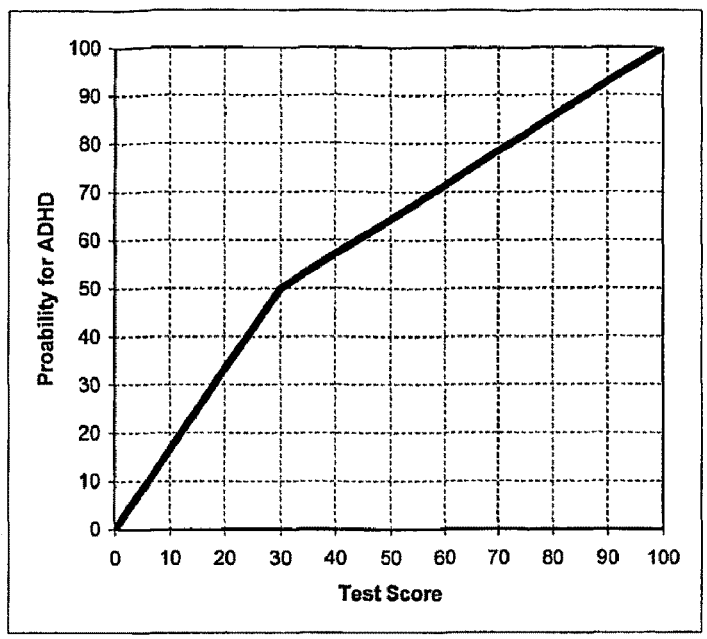
Figure 3B:
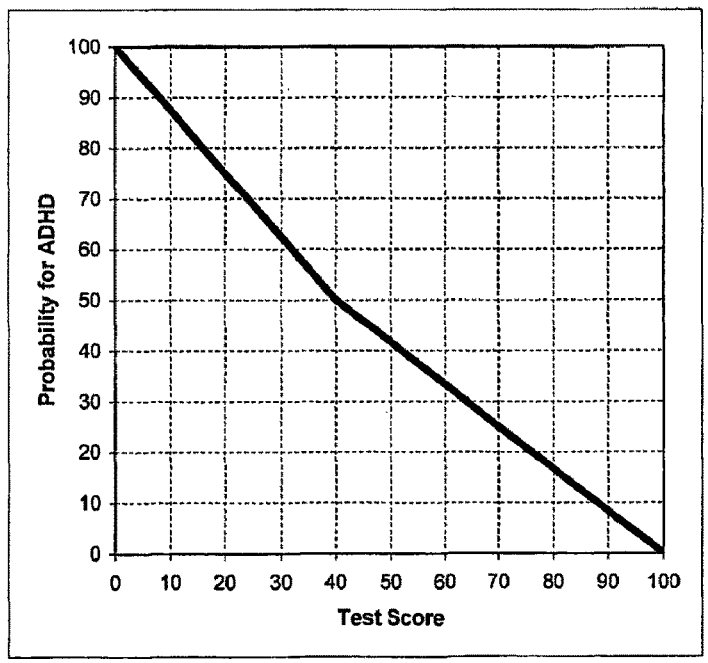

FIGS. 3(A)-(B) are graphical representations of the standardization process for the WURS scale and the Consistency Index (CI), respectively.

FIG. 4 schematically illustrates the general structure of the sequential assessment of ADHD of an embodiment of the present invention.

FIG. 5 schematically presents an aspect of an embodiment of the present invention process of increasing of the precision of assessment along the steps of the Bayesian model across all studies.

DETAILED DESCRIPTION OF THE INVENTION

A first aspect of an embodiment of the present invention is directed to a method, apparatus, or computer program product for assessing an individual for disorders associated with attentional impairments.

The method comprises (1) obtaining the scores of two or more assessment instruments for attentional impairment by administering the instruments to an individual; (2) calibrating the scores obtained from the assessment instruments by standardizing the scores; and (3) operating upon the calibrated scores using a computational procedure, producing a composite result.

The assessment instruments used can be of any type, including, but not limited to: demographic questionnaires, behavioral checklists, psychometric tests, parent reports, teacher rating forms, or EEG-based vigilance, attention, and consistency measures. The EEG-based measures may include among others the Consistency Index, Alpha Blockade Index, or both.

The score calibration and standardization process maps the scores from the assessment instruments to a particular range. The range is not limited by the invention and will be chosen by one skilled in the art as appropriate to the particular embodiment practiced. A typical standardization would map the assessment instrument scores to conditional probabilities ranging from zero to one.

The standardization process can further include, if desirable, the mapping of indeterminate scores from the assessment instruments to a particular score within the standardization range. For example, using the scale of conditional probabilities described above, an indeterminate result from an assessment instrument could be mapped to a conditional probability of 0.5. One skilled in the art will appreciate that the range of scores from an assessment instrument constituting an indeterminate result can be adjusted as necessary to achieve a particular likelihood of diagnostic error. The same likelihood of diagnostic error, if applied to each of the disparate assessment instruments, will produce a composite result with a likelihood of diagnostic error lower than any of the individual assessment instruments. The likelihood of diagnostic error for the composite result can be controlled in this manner. Some embodiments of the present invention may use as the preset likelihood of error a likelihood of error within the range of 0.01 to 0.1.

The final step in practicing the method taught by an embodiment of the present invention is the operation upon the calibrated scores using a computational procedure. The computational procedure chosen might include, but is not limited to, the following: a sequential Bayesian inference procedure, computation of joint probability distribution, multiplication of probabilities, logical expression, or a combination thereof.

Figure 1:
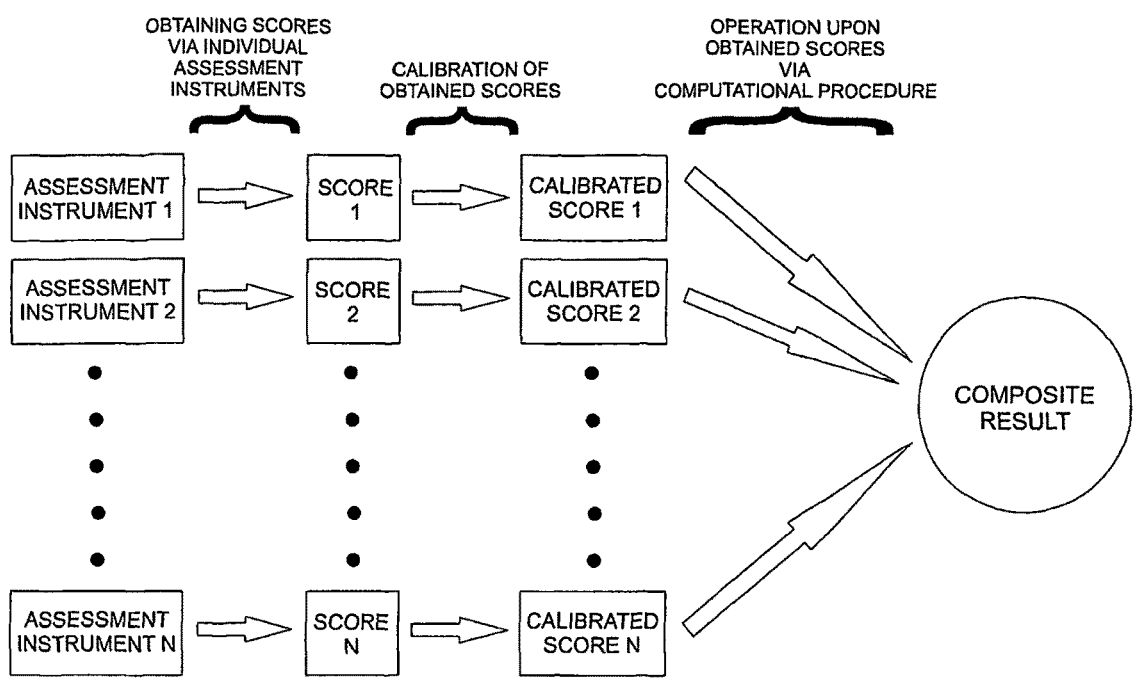
FIG. 1 is a diagram of the general structure of an embodiment of the present invention and its components.

Turning to FIG. 1, FIG. 1 schematically illustrates a conceptual block diagram of an embodiment of the present invention. In this diagram, SCORES are obtained from two or more ASSESSMENT INSTRUMENTS, numbered one (1) through N. This process is denoted OBTAINING SCORES VIA INDIVIDUAL ASSESSMENT INSTRUMENTS and is performed according to the method required by each individual assessment instrument. The scores obtained are then calibrated to produce CALIBRATED SCORES. This process is denoted on the diagram CALIBRATION OF OBTAINED SCORES and is described in detail below. Finally, a computational procedure is used to produce a COMPOSITE RESULT from the calibrated scores. This process is denoted OPERATION UPON OBTAINED SCORES VIA COMPUTATIONAL PROCEDURE, and is described in detail below.

Another aspect of an embodiment of the present invention is an apparatus or computer program product designed to perform the method described above. The apparatus might be a microprocessor or other processing unit.

Figure 2:
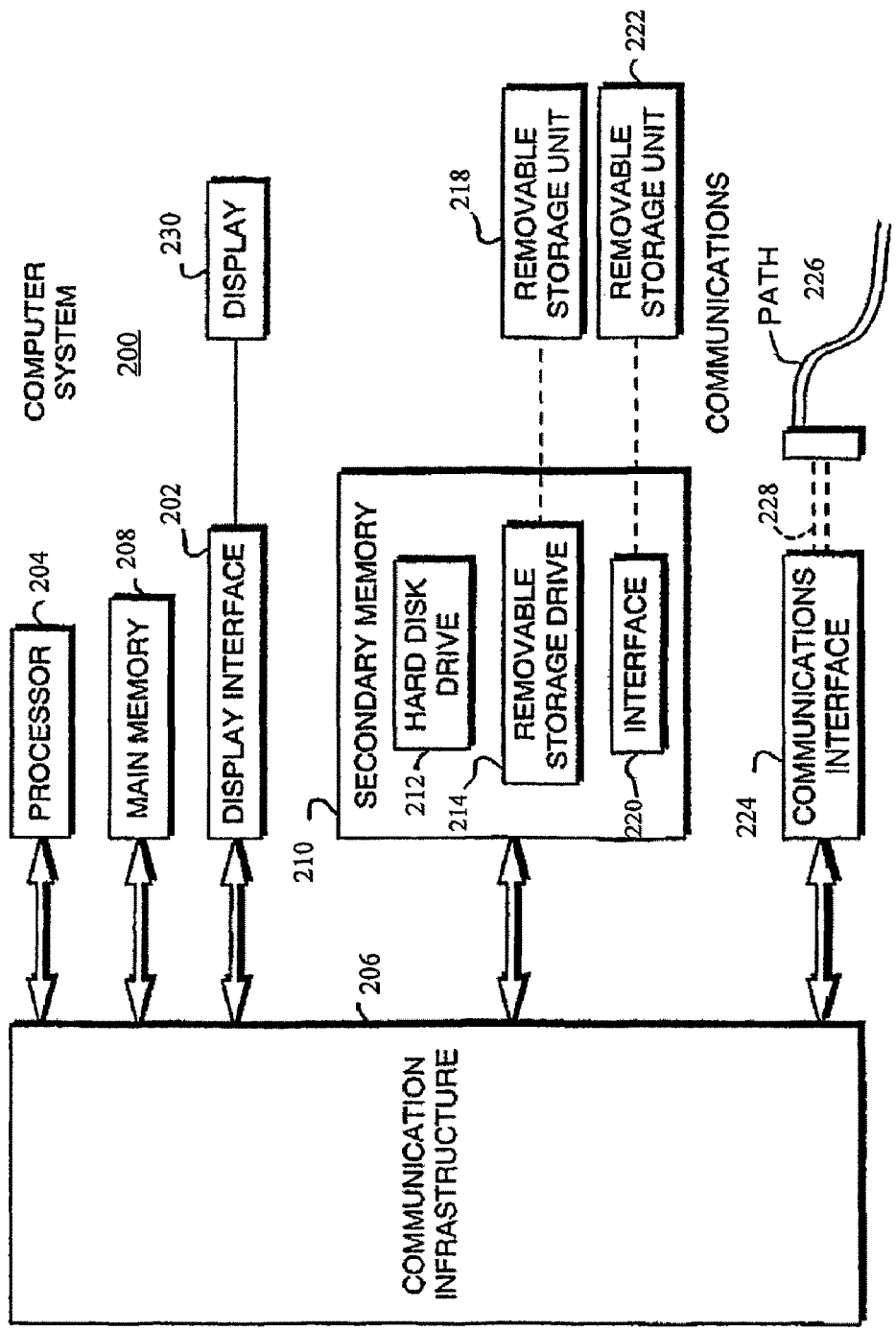
FIG. 2 is a functional block diagram for an illustrative computer system for implementation of the present invention.

The method and apparatus of an embodiment of the present invention (as discussed throughout this document) may be implemented using hardware, software or a combination thereof and may be implemented in one or more computer systems or other processing systems, or partially performed in processing systems such as personal digit assistants (PDAs). In an example embodiment, the invention was implemented in software running on a general-purpose computer 200 as illustrated in FIG. 2. Computer system 200 includes one or more processors, such as processor 204. Processor 204 is connected to a communication infrastructure 206 (e.g., a communications bus, crossover bar, or network). Computer system 200 includes a display interface 202 that forwards graphics, text, and other data from the communication infrastructure 206 (or from a frame buffer not shown) for display on the display unit 230.

Computer system 200 also includes a main memory 208, preferably random access memory (RAM), and may also include a secondary memory 210. The secondary memory 210 may include, for example, a hard disk drive 212 and/or a removable storage drive 214, representing a floppy disk drive, a magnetic tape drive, an optical disk drive, etc. The removable storage drive 214 reads from and/or writes to a removable storage unit 218 in a well-known manner. Removable storage unit 218, represents a floppy disk, magnetic tape, optical disk, etc. which is read by and written to by removable storage drive 214. As will be appreciated, the removable storage unit 218 includes a computer usable storage medium having stored therein computer software and/or data.

In alternative embodiments, secondary memory 210 may include other means for allowing computer programs or other instructions to be loaded into computer system 200. Such means may include, for example, a removable storage unit 222 and an interface 220. Examples of such removable storage units/interfaces include a program cartridge and cartridge interface (such as that found in video game devices), a removable memory chip (such as a ROM, PROM, EPROM or EEPROM) and associated socket, and other removable storage units 222 and interfaces 220 which allow software and data to be transferred from the removable storage unit 222 to computer system 200.

Computer system 200 may also include a communications interface 224. Communications interface 224 allows software and data to be transferred between computer system 200 and external devices. Examples of communications interface 224 may include a modem, a network interface (such as an Ethernet card), a communications port, a PCMCIA slot and card, etc. Software and data transferred via communications interface 224 are in the form of signals 228 which may be electronic, electromagnetic, optical or other signals capable of being received by communications interface 224. Signals 228 are provided to communications interface 224 via a communications path (i.e., channel) 226. Channel 226 carries signals 228 and may be implemented using wire or cable, fiber optics, a phone line, a cellular phone link, an RF link and other communications channels.

In this document, the terms "computer program medium" and "computer usable medium" are used to generally refer to media such as removable storage drive 214, a hard disk installed in hard disk drive 212, and signals 228. These computer program products are means for providing software to computer system 200. The invention includes such computer program products.

Computer programs (also called computer control logic) are stored in main memory 208 and/or secondary memory 210. Computer programs may also be received via communications interface 224. Such computer programs, when executed, enable computer system 200 to perform the features of the present invention as discussed herein. In particular, the computer programs, when executed, enable processor 204 to perform the functions of the present invention. Accordingly, such computer programs represent controllers of computer system 200.

In an embodiment where the invention is implemented using software, the software may be stored in a computer program product and loaded into computer system 200 using removable storage drive 214, hard drive 212 or communications interface 224. The control logic (software), when executed by the processor 204, causes the processor 204 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above were implemented in Java, but could be implemented in other program languages, such as C++, that would be appreciated by those skilled in the art.

A fourth aspect of an embodiment of the present invention is an apparatus designed to perform the calibration and computation steps of the method described above, using scores obtained from two or more assessment instruments for attentional impairment, conducted on an individual. The apparatus might be a microprocessor or other processing unit. Any device capable of carrying out the mathematical manipulation required by the method could be configured to perform the steps. FIG. 2 is a block diagram of a representative computer system that could be used to practice the invention.

EXAMPLES

Practice of various embodiments will be still more fully understood from the following examples, which are presented herein for illustration only and should not be construed as limiting the invention in any way.

Example No. 1

Application of an Embodiment

The diagnosis of many mental health disorders can be difficult and controversial to make, primarily because the majority of diagnostic approaches to mental disorders are based upon subjective reports of symptoms. Although almost all mental disorders are considered to be manifestations of biological, psychological, and environmental components within one individual, all of these domains are rarely thoroughly assessed and simultaneously incorporated into the diagnostic process. Even if all domains are assessed, the evaluations often lead to incomplete or conflicting data or "gray zones," where the diagnosis is not clear, and where clinicians are forced to make a dichotomous diagnosis, based primarily upon their own subjective clinical judgment. This is a particular problem when diagnosing ADHD, since no laboratory or psychological test or battery is available that provides sufficient sensitivity and specificity of diagnosis. This problem is made more urgent by the fact that early recognition, assessment, and management of this condition can redirect the educational and psychosocial development of most children with ADHD, thereby having a significant impact upon the well-being of a child accurately diagnosed with ADHD. Presented in this section is an exemplary embodiment of the present invention, a probabilistic method using a sequential Bayesian decision-making computational procedure, which allows the results of multiple tests to produce a single assessment that is more precise and with a smaller gray zone of unclassified cases than its individual components. The method is designed in a way that keeps the likelihood of diagnostic error below a certain preset probability.

Obtaining Scores from Assessment Instruments

Various embodiments of the present invention encompass the use of scores from two or more assessment instruments, the use of which will be understood by one skilled in the art. Information and details about the assessments referenced in the herein-described embodiment of the invention are listed below.

ADHD Symptom Inventory (ADHD-SI). The ADHD-Symptom Inventory is an 18-item scale developed from DSM-IV criteria for ADHD and was introduced by Cox, et al. (1999). The ADHD-SI has good test-retest reliability ($r=0.87$, $p<0.005$). In addition, the ADHD-SI correlates highly with the Hyperactivity Index of the Conners' ($r=0.72$, $p=0.044$), the Attention Problems subscale of the Achenbach's Child Behavior Checklist ($r=0.82$, $p=0.013$), and the Impulsivity-Hyperactivity subscale of the Conners' ($r=0.88$, $p=0.004$). Additionally, in previous research the ADHD-SI discriminated between diagnostic status the most strongly ($t=3.7$, $p<0.01$) among the four psychometrics with no overlap in scores (See Cox, D. J., Kovatchev, B. P., Morris, J. B., Phillips, C., Hill, R., & Merkel, L. (1999), "Electroencephalographic and Psychometric Differences Between Boys with and without Attention-Deficit/Hyperactivity Disorder (ADHD): A Pilot Study," Applied Psychophysiology and Biofeedback, 23, 179-188, of which is hereby incorporated by reference in it's entirety; See Merkel, R. L., Cox, D. J., Kovatchev, B. P., Morris, J., Seward, R., Hill, R., & Reeve, R. (2000), "The EEG Consistency Index as a Measure of Attention Deficit/Hyperactivity Disorder and Responsiveness to Medication: A Double Blind Placebo Controlled Pilot Study," Applied Psychophysiology and Biofeedback, 25, 133-142), of which is hereby incorporated by reference herein in its entirety).

DuPaul AD/HD Rating Scale-IV Inattentive Type. The AD/HD Rating Scale-IV is similar to the ADHD-SI, both scales being developed independently and concurrently at different laboratories. This rating scale has demonstrated adequate reliability and validity (See DuPaul, G. J., Power T. J., Anastopoulos, A. D., Reid, R. (1998), "ADHD Rating Scale-IV Checklists, Norms, and Clinical Interpretation," New York: Guilford Press, of which is here by incorporated by reference herein in its entirety). The scale items reflect the DSM-IV criteria and respondents are asked to indicate the frequency of each symptom on a 4-point Likert scale. The Home and School Versions of the scale both consist of two subscales: Inattention (nine items) and Hyperactivity-Impulsivity (nine items). The manual provides information regarding the factor analysis procedures to develop the scales, as well as information regarding the standardization, normative data, reliability, validity, and clinical interpretation of the scales (See DuPaul, et al., 1998).

Wender-Utah Rating Scale (WURS). The WURS test is a 61-item retrospective self-report scale where individuals rate the severity of ADHD symptoms experienced when they were children using a 5-point Likert scale. For adults, WURS has been shown to be a valid retrospective screening and dimensional measure of childhood ADHD symptoms (See Stein, M. A., Fischer, M., Szumowski, E. (2000), "Evaluation of Adults for ADHD: Erratum," Journal of the American Academy of Child and Adolescent Psychiatry, 39, 674, of which is hereby incorporated by reference herein in it's entirety), to replicate and correlate with Connors Abbreviated Parent and Teacher Questionnaire and demonstrate internal consistency reliability (See Fossati, A., Di Ceglic, A., Acquarini, E., Donati, D., Donini, M., Novella, L. & Maffei, C. (2001), "The Retrospective Assessment of Childhood Attention-Deficit Hyperactivity Disorder in Adults: Reliability and Validity of the Italian Version of the Wender Utah Rating Scale," Comprehensive Psychiatry, 42, 326-336, of which is hereby incorporated by reference herein in its entirety), and to exhibit good construct validity (See Weyandt, L. L., Linterman, I., & Rice, J. A. (1995), "Reported Prevalence of Attentional Difficulties in a General Sample of College Students," Journal of Psychopathological and Behavioral Assessment, 17, 293-304, of which is hereby incorporated by reference herein in its entirety).

EEG Consistency Index (EEG-CI). The EEG-CI is an EEG-based measure of ADHD (See Cox, et al., 1999; See Kovatchev, et al., 2001; See Kovatchev, B. P., Cox, D. J., Hill, R., Reeve, R., Robeva, R. S., & Loboschefski, T. (2001), "A Psychophysiological Marker of Attention Deficit/Hyperactivity Disorder—Defining the EEG Consistency Index," Applied Psychophysiology and Biofeedback, 26, 127-139, of which is hereby incorporated by reference herein in its entirety; and See Merkel, et al., 2000). The CI ranges from 0 to 100 percent; a CI<40 percent indicates ADHD (See Kovatchev, et al., 2001). The CI of a person is computed using data from two adjacent disparate cognitive tasks. The CI is based on the notion that the EEG data stream can be represented by a three-dimensional numeric array—at any given moment one dimension is frequency of brain waves, another is spatial—the location of the electrode on a subject's head, and the third is time. ADHD can cause disruption in the frequency or spatial dimension or in both. This disruption is most evident when the tested subject transitions from one cognitive task to another, the two tasks being separated by a rest period of approximately 3-5 minutes. The transition is deemed "consistent" if the differences between the means of the power spectra from the adjacent tasks shift coherently from low to high or vice versa, e.g. a consistent transition would mean that most frequency bands and most channels would display similar unidirectional shifts, while an inconsistent, transition will result in scattered power changes across the EEG bands and channels. We used the previously published algorithm with threshold parameter of 1.0 and no cutoff (Kovatchev, et al., 2001). These settings correspond to the procedures employed by previous studies (See Cox, et al., 1999; Kovatchev, et al., 2001; and Merkel, et al., 2000). Details can be found in the above referenced articles.

Indeterminate Scores, "Gray Zones," and Misclassification Rate of a Test

Assume that a particular assessment instrument of a condition produces a certain score for each tested individual, and a higher score implies a greater likelihood of that condition, a lower score indicates that the condition is unlikely, and a score between certain numbers x, y indicates that the score is indeterminate. In this setting, the interval [x, y] is the "gray zone" of the test. β is the relative size of the gray zone of our test, e.g. β is the probability that a person may remain unclassified after administering the test because his/her score is between x and y. Another important characteristic of the test is its probability for a misclassification α; in our setting α is the probability that a person with a high score would be classified as not having the condition, or a person with low score would be classified as having the condition. It is intuitively clear that α and β are inversely related—if we want to hold the misclassification rate α below a certain number, the likelihood that a person cannot be classified β increases. In other words, if we insist on certainty of the classification (1−α), the percentage of cases β that cannot be classified with that certainty will increase. Thus at a fixed error rate α, a test with a larger gray zone probability β would be less comprehensive than a test with a smaller β (See Kovatchev, Boris; Penberthy, Jennifer Kim; Robeva, Raina, Breton, Marc; and Cox, Daniel, (2004-2005) "Computational Strategies in the Evaluation of Attention Deficit/Hyperactivity Disorder (ADHD)," *Attention Deficit Hyperactivity Disorder (ADHD) Research*, pp 1-35, Nova Science Publishers, Inc. Hauppauge, N.Y., of which is hereby incorporated by reference herein in its entirety). Consequently, if a combination of assessment instrument scores produces a result with a gray zone smaller than each individual assessment instrument, while keeping the error rate below a fixed α, such a combination would be more comprehensive than each of its individual components.

Standardizing the Scores of Different Assessment Instruments

In order to integrate the data from the disparate assessment instruments into a single result, the output of these assessment instruments must be standardized. In order to do so, the output of each test is translated into a probability for ADHD. The idea is that at each step of the overall assessment, each subject receives a certain score on each instrument and the magnitude of this score depends on whether the subject has ADHD, as well as on the severity of the disorder. In other words, the probability of earning a certain score depends on the subjects' condition, ADHD or non-ADHD. In addition, each test has a suggested cutoff value, and scores greater (or lower) than this cutoff value are accepted as indicators of ADHD. Thus, for each test we can define a function that represents the conditional probability of earning the specified score, given ADHD. The standardization process described in this embodiment of the invention uses linear mappings of a test score into a [conditional] probability ranging from 0 to 1 with the test cutoff value mapped to 0.5, and the test maximal (or minimal) value indicating ADHD mapped to 1. If the test has a gray zone (a range of indeterminate scores), then the entire gray zone is mapped to a probability of 0.5. Several examples will clarify the test score standardization:

1) ADHD-Symptom Inventory: The score on the ADHD-SI ranges from 0 to 36 with scores>12 indicating ADHD. The mapping formula is then:

$$\begin{cases} x \leq 12 & P(ADHD \mid x) = \frac{x}{24} \\ x \geq 12 & P(ADHD \mid x) = \frac{x}{48} + \frac{1}{4} \end{cases}$$

2) DuPaul AD/HD Rating Scale-IV Inattentive Type: The score ranges from 0 to 100 with scores>93 indicating ADHD. The mapping formula is then:

$$\begin{cases} x \leq 93 & P(ADHD \mid x) = \frac{x}{186} \\ x > 93 & P(ADHD \mid x) = \frac{x}{14} - \frac{43}{7} \end{cases}$$

3) WURS scale: The score ranges from 0 to 100 with scores>30 indicating ADHD. The mapping formula is then:

$$\begin{cases} x \leq 30 & P(ADHD \mid x) = \frac{x}{60} \\ x > 30 & P(ADHD \mid x) = \frac{x}{140} + \frac{2}{7} \end{cases}$$

4) The EEG Consistency Index (CI): The Consistency Index ranges from 0 to 100 percent with a CI<40 percent indicating ADHD. The mapping formula is then:

$$\begin{cases} x \leq 40 & P(ADHD \mid x) = 1 - \frac{x}{80} \\ x > 40 & P(ADHD \mid x) = \frac{5}{6} - \frac{x}{120} \end{cases}$$

5) The Alpha Blockade Index (ABI): The ABI ranges from 0 to 100 percent with an ABI<20 percent indicating ADHD. The mapping formula is then:

$$\begin{cases} x \leq 20 & P(ADHD \mid x) = 1 - \frac{x}{40} \\ x > 20 & P(ADHD \mid x) = \frac{5}{8} - \frac{x}{160} \end{cases}$$

6) DuPaul AD/HD Rating Scale-IV Hyperactive/Impulsive Type: scores range from 0 to 100 with scores>98 indicating ADHD. The mapping formula is then:

$$\begin{cases} x \le 98 & P(ADHD|x) = \dfrac{x}{196} \\ x > 98 & P(ADHD|x) = \dfrac{x}{4} - 24 \end{cases}$$

Turning to FIG. 3, in order to visualize the standardization procedure, FIGS. 3(A) and 3(B) graphically illustrate examples of the test score standardization of the WURS scale and the Consistency Index (CI), respectively.

Computational Operation upon the Calibrated Scores

In an exemplary embodiment, once the standardization of scores from the assessment instruments is completed, a Bayesian computational procedure for calculating the probability for ADHD for each individual operates upon the results from the individual assessments to produce a composite result. An outline for this computational procedure is shown below.

The procedure works as follows: At step 0, a prior probability for ADHD P0ADHD=0.5 is assigned to each subject regardless of whether she is ADHD or control. Then, after the first test $P_1^{test}=P(ADHD/\text{test score})$ and $P_2^{test}=1-P_1$ are used to calculate a posterior probability $P^1_{ADHD}$ for ADHD, using the formula:

$$P^1_{ADHD} = \frac{P_1^{test} \cdot P^0_{ADHD}}{P_1^{test} \cdot P^0_{ADHD} + P_2^{test} \cdot (1 - P^0_{ADHD})}$$

From here on the procedure is recursive—after each step the posterior probability becomes a prior probability for the next step; e.g. in the formula above $P^0_{ADHD}$ is replaced by $P^1_{ADHD}$, $P_1^{test}$ and $P_2^{test}$ derived from the second test, etc. In general, the posterior probability from step (n−1) becomes a prior probability in step (n) and then posterior probability is computed for step (n) using the results from the assessment at step (n). At each step we may have a "gray zone" of indeterminate assessment, however, at each sequential step the gray zone will become smaller and the final result is substantially more precise than any of its individual steps. The final result of the computational procedure (here, the Bayesian algorithm) is a probability for ADHD assigned to each subject (0 to 100 percent), e.g. a placement of each subject on a continuum of disruption, with greater number and severity of disruptions resulting in placement on the high extreme end of the continuum. As described here, various embodiments may provide, but are not limited to providing, increased specificity/sensitivity beyond individual assessment instruments.

Figure 4A:
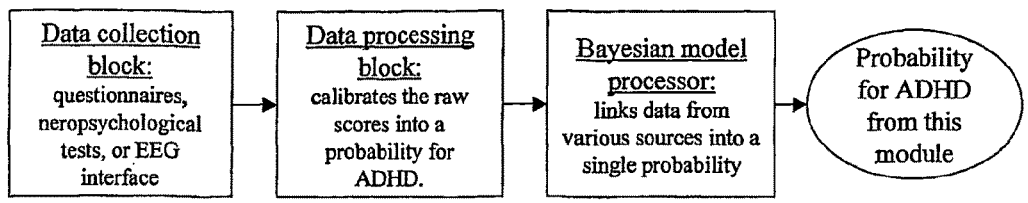
Figure 4B:
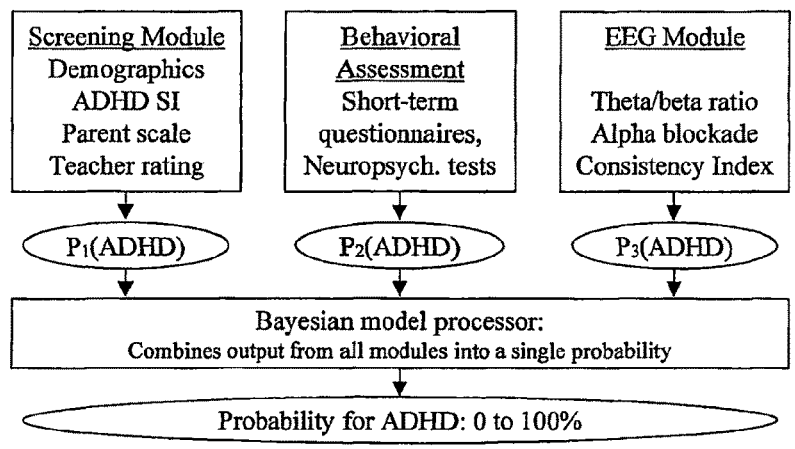

FIG. 4 schematically illustrates the general structure of the sequential assessment of ADHD of an embodiment of the present invention. Each module of the assessment has the unified internal structure presented in FIG. 4(A). The screening module would typically include input from demographic characteristics (e.g. age, gender) and several questionnaires screening for ADHD, such as ADHD SI, parent survey, teacher report, etc. The screening module produces an initial estimate of the probability for ADHD of the screened person even if only one of the questionnaires is completed. Each additional questionnaire will update and refine this estimate using our Bayesian model. The short-term behavioral assessment would typically include questionnaires and neuropsychological tests, which would allow for testing of the effectiveness of a medication, dose adjustment, etc. The EEG assessment would include several potential markers of ADHD, in particular our Consistency Index (CI) (See Kovatchev, et al., 2001), the Alpha Blockade Index (See Robeva R., Penberthy J. K., Loboschefski T., Cox D., Kovatchev B. "Sequential Psycho-Physiological Assessment of ADHD: A Pilot Study of Bayesian Probability Approach Illustrated by Appraisal of ADHD in Female College Students," Applied Psychophysiology and Biofeedback, 28, 2003, of which is hereby incorporated by reference herein in its entirety) and the Attentional Index (ratio of theta/beta, which is reported in the literature as a marker of ADHD (See Monastra V. J., Lubar J. F., Linden M., VanDeusen P., Green G., Wing W., Phillips A., Fenger T. N., "Assessing Attention Deficit Hyperactivity Disorder via Quantitative Electroencephalography: An Initial Validation Study," Neuropsychology 13:424-433, 1999, of which is hereby incorporated by reference herein in its entirety). The combination of the results from different tests within each module follows the Bayesian algorithm described above.

The result of each module is a probability for ADHD. Then, as schematically presented in FIG. 4(B), the combination of results across all modules into a single assessment of ADHD.

The modular design of this system allows for a separate utilization of a screening, or screening+behavioral assessment modules, if EEG system is unavailable in some settings. This design also allows for inclusion of future ADHD screening technologies. For example, data from a motion detector recording the movement of a subject's head during a task could be included if proven valuable in the assessment of ADHD.

Results of Combining the Scores of Different Tests

The exemplary embodiment includes applying this method to the data from studies I-V described below, including behavioral rating scales and EEG assessments.

Study Subjects—During the past several years we have conducted a series of studies investigating EEG patterns associated with ADHD:

Study I: Four boys, ages 6-10, with ADHD (one primarily inattentive type, one primarily hyperactive/impulsive type, and two combined type) and four age-matched control boys had their EEG data acquired during two 30-minute tasks (video and reading) separated by a 5-minute break. Parents completed the ADHD-SI [19]. ADHD subjects were regularly taking methylphenidate for their symptoms, but were off the medication during assessment. For the ADHD boys, this procedure was repeated three months later, to assess test-retest reliability. Two of the boys with ADHD were Caucasian, one was African-American, and one was Indian. All four of the control subjects were Caucasian. No subjects reported co-morbid diagnoses or learning disabilities. Results are reported by Cox, et al. [19].

Study II: Seven ADHD males (four primarily inattentive type, and three combined type) and six non-ADHD males, ages 18-25, participated in a double-blind, placebo versus methylphenidate controlled crossover design study. ADHD subjects had to have previously taken methylphenidate but could not be taking any medication for their condition within the six months prior to the study. EEG data was acquired while the subjects were given four tasks of the Gordon Diagnostic System, two easy (auditory and visual) and two hard (auditory and visual). Subjects and their parents completed the ADHD-SI [19]. Two of the subjects were African-American, and one control subject was Asian, all others were Caucasian. No. subjects had co-morbid diagnoses or learning disabilities. Results are reported by Merkel, et al. (See Merkel R. L., Cox D. J., Kovatchev B., Morris J., Jr., Seward R., Hill R., Reeve R., "The EEG Consistency Index as a Measure of ADHD and Responsiveness to Medication: A Double Blind Placebo Controlled Pilot Study," Appl. Psychophysiol. Biofeedback 25:133-142, 2000, of which is hereby incorporated by reference herein in its entirety) and Cox, et al. (See Cox D. J., Merkel R. L.; Kovatchev B., Seward R., "Effect of Stimulant Medication on Driving Performance of Young Adults with Attention-deficit Hyperactivity Disorder: A preliminary Double-blind Placebo Controlled Trial," Journal of Nervous and Mental Disorders, 188, 230-234, 2000, of which is hereby incorporated by reference herein in its entirety).

Study III: Eighteen boys and 17 girls, ages 8-16, classified as either ADHD or non-ADHD (9 boys and 8 girls with ADHD-combined type and 9 boys and 9 girls without ADHD) had EEG data collected for 36 minutes while performing various tasks. Parents and teachers completed the Conners' Rating Scale (See Conners C. K., "Conners' Rating Scales—Revised; technical Manual," North Tonawanda, N.Y.: Multi-Health Systems, 1997, of which is hereby incorporated by reference herein in its entirety), Achenbach Child Behavior Checklist (See Achenbauch, T. M., & Edelbrock, C., "Manual for the Child Behavior Checklist," Burlington, Vt.: University of Vermont Department of Psychiatry, 1983, of which is hereby incorporated by reference herein in its entirety), and the ADHD-SI [19]. All subjects were Caucasian with the exception of one child in the control group who was Hispanic. All ADHD subjects were taking a stimulant medication Computational Strategies in the Evaluation of ADHD 9 (with the exception of Cylert) to treat their symptoms, but were taken off their medication 24 hours prior to being tested. One ADHD subject reported having dyslexia, but no additional co-morbidities were reported or diagnosed. Results are reported by Kovatchev, et al. (See Kovatchev, et al., 2001).

Study IV was conducted at Sweet Briar College to study female college students with ADHD. The participants engage in a series of short concentration tasks (2-3 min.) with shorter resting intervals (1-2 min). Subjects are administered the ADHD-SI [19], and the Wender-Utah Rating Scale (WURS) (See Ward M. F., Wender P. H., Reimherr F. W., "The Wender Utah Rating Scale: An Aid in the Retrospective Diagnosis of Childhood Attention Deficit Hyperactivity Disorder," Am. J. Psychiatry 150:885-890, 1993, of which is hereby incorporated by reference herein in its entirety), which is a 61-item retrospective self-report scale with adequate reliability and validity. We currently have collected data for 6 ADHD Caucasian females (all ADHD-combined type) and 6 non-ADHD Caucasian females. No subjects reported any co-morbid disorders or learning disabilities. Results are reported by Robeva, et al. (See Robeva R., Penberthy J. K., Loboschefski T., Cox D., Kovatchev B., "Sequential Psycho-Physiological Assessment of ADHD: A Pilot Study of Bayesian Probability Approach Illustrated by Appraisal of ADHD in Female College Students," Applied Psychophysiology and Biofeedback, 28, 2003, of which is hereby incorporated by reference herein in its entirety).

Study V: Seventy-seven children ages 8-12 (67 males and 10 females, 36 ADHD and 41 non-ADHD) were administered EEGs while watching a movie for 20 minutes, resting with eyes open for 5 minutes, reading silently for 10 minutes, resting with eyes open for 5 minutes, then performing creative drawing tasks for 10 minutes. This pattern was repeated once, for a total test time of 100 minutes. Parents and teachers were administered the DuPaul AD/ED Rating Scale-IV [20], and parents completed the ADHD-SI [19]. Subjects included two African-American males, one Indian male, and two subjects who did not specify their ethnicity. All other subjects were Caucasian. Twelve ADHD subjects were diagnosed as primarily inattentive type, one as primarily hyperactive/impulsive type, and the remainder (23) met criteria for ADHD-combined type. Co-morbid disorders in the ADHD groups included: specific phobia (7); oppositional defiant disorder (8); obsessive-compulsive disorder (1); enuresis (1): and 1 subject with separation anxiety disorder and ODD, and 1 subject with social phobia and GAD. Co-morbid disorders in the control group included: specific phobia (1) and enuresis (1). Results are first reported in this chapter.

Study VI: Six males diagnosed with ADHD (four primarily inattentive type and two combined type ADHD), were administered EEGs while on and off methylphenidate. The EEGs were acquired while the subjects viewed a movie for 20 minutes, rested with eyes open for 5 minutes, and read silently for 10 minutes. Parents and teachers were administered the DuPaul AD/HD Rating Scale-IV [20]. Subjects were between the ages of 16-21, and reported a previous positive response to methylphenidate. All subjects were Caucasian. One subject met diagnostic criteria for social phobia and one subject met criteria for oppositional defiant disorder. Three subjects reported that they had been diagnosed with learning disorders, such as dyslexia. Results are first reported in this chapter.

TABLE 1

Probabilities for ADHD within each study for each test

| Study | | ADHD-SI | WURS | DuPaul (I) | CI | Combined probability |
|---|---|---|---|---|---|---|
| I | ADHD | 0.63 | — | — | 0.79 | 0.78 |
| | Control | 0.04 | | | 0.24 | 0.014 |
| | p-level | 0.0146 | | | 0.01 | 0.0009 |
| II | ADHD | 0.7 | — | — | 0.88 | 0.93 |
| | Control | 0.16 | | | 0.57 | 0.21 |
| | p-level | 0.0008 | | | 0.095 | 0.0024 |
| III | ADHD | 0.86 | — | — | 0.81 | 0.94 |
| | Control | 0.19 | | | 0.51 | 0.24 |
| | p-level | 0 | | | 0.0019 | <0.0005 |
| IV | ADHD | — | 0.56 | — | 0.83 | 0.84 |
| | Control | | 0.18 | | 0.18 | 0.033 |
| | p-level | | 0.0029 | | 0.0019 | <0.0005 |
| V | ADHD | — | — | 0.68 | 0.65 | 0.74 |
| | Control | | | 0.19 | 0.54 | 0.29 |
| | p-level | | | <0.0005 | 0.19 | <0.0005 |

Table 1 presents the probabilities for ADHD estimated by each test for ADHD vs. Control subjects. T-tests compare these probabilities within each study. As evident from Table 1, although a number of tests reach significance in most studies, a correction for the significance level accounting for multiple parallel tests would eliminate many significant results. The last column of Table 1 (Combined probability) presents the joint results from ADHD questionnaire plus EEG assessment within each study, computed using our Bayesian algorithm. It is should be appreciated that a combination of tests within a study generally provides a better ADHD-control separation than each individual test (in terms of a smaller p-value).

Combining the Results from Different Studies

Most studies alone had a small sample focused on a specific age/gender group, e.g. 8 boys ages 6-10. Thus, some analyses, such as gender or age comparisons, were not possible within any particular study. However, the standardization of each study results into the same scale, probability for ADHD, allows for combination of the data across studies. When standardized and combined, the data resulted in a clear separation between ADHD vs. non-ADHD groups in males below the age of 16 (p<0.001), males above the age of 16, (p=0.015), females below the age of 16, (p=0.0014), and females above the age of 16, (p=0.0022). Specifically, Table 2 presents the means and the standard deviations for each cross-section of the combined across studies population. The black bars in the second row of Table 2 indicate subject groups that cannot be differentiated at P=0.05 It is evident that the control population were quite homogeneous—there are no groups different in terms of their probabilities for ADHD. The ADHD population however, was not internally homogeneous: while boys and girls under the age of 16 were similar, and girls under 16 were similar to boys above 16, girls above 16 stand alone as a separate subgroup, which is somewhat closer to controls in terms of its probability for ADHD. Such previously unrecognized results were made possible by the use of cross-study standardization of the data.

TABLE 2

Cross-Sectional Probabilities for ADHD and Cross-Sectional Similarities

| | ADHD | | | | Control | | | |
|---|---|---|---|---|---|---|---|---|
| | Age <16 years | | Age >16 years | | Age <16 years | | Age >16 years | |
| | Boy | Girl | Boy | Girl | Boy | Girl | Boy | Girl |
| Probability for ADHD (%) | 80% | 87% | 93% | 67% | 23% | 32% | 21% | 30% |
| Cross-Sectional Similarities | ■ | | | | | | | |
| | | ■ | | | | | | |
| | | | | | | ■ | ■ | ■ |

Finally, FIG. 5 schematically presents an aspect of an embodiment of the present invention process of increasing of the precision of assessment along the steps of the Bayesian model across all studies. This standard Box plot presents the median, 50% of the distribution, and outliers. It is evident that with the application of consecutive test the differentiation between ADHD and No-ADHD groups increases, achieving a best separation at the end of the procedure. FIGS. 5(A), 5(B) and 5(C) graphically represent the subject distribution after test one, tests one and two, and tests one, two and three, respectively.

In summary, this exemplary embodiment presents several mathematical models and the results from six consecutive studies revealing various parameters of ADHD-related disruption at psychological, behavioral, and physiological levels. Overall, such a method and system of the embodiment has optimized both our data acquisition procedures with respect to EEG, our theoretical development of mathematical models of EEG consistency, and our choice and method of psychological and behavioral assessments. A first set of models discussed here refers to procedures maximizing the assessment of inconsistency in EEG waves on a temporal level of half-hour, minutes, and seconds. Various data sets (ours and by others) support the utility of each of these scales in various subpopulations. For example, the Consistency Index (CI) works best in boys below the age of 16, while the Alpha Blockade Index is a good marker of ADHD in college-age females. However, none of these individual measures, and none of the widely used psychometric measures, achieve a perfect assessment of ADHD when used in isolation, nor do they adequately evaluate the impact of a medication. For this reason, the present invention method has developed and successfully pilot tested a sequential stochastic model combining behavioral and biologic data for classification of participants with and without ADHD, and demonstrated that several imperfect tests can successfully be combined into a comprehensive assessment that is more powerful than its individual components. Thus, the present invention embodiment provides an integrated multi-method psycho-physiological ADHD assessment procedure, based upon a theoretical model of disruption of self-regulation and empirically supported by research experience and findings.

Example No. 2

In particular, a first aspect of an exemplary embodiment of the present invention is directed to a method, apparatus, and/or computer program product for assessing individuals for disorders associated with attentional impairments. The related method and apparatus comprises (a) obtaining scores from two or more assessment instruments for attentional impairment, conducted on an individual, (b) calibrating the obtained scores by standardizing the range of obtainable scores for each of the instruments, and (c) operating upon the calibrated scores using a computational procedure to produce a composite result. The assessment instruments may include, for example, two or more of the following: demographic questionnaires, behavioral checklists, psychometric tests, parent reports, teacher rating forms, or EEG-based vigilance, attention, and consistency measures. Also, the assessment instruments may include the Consistency Index, Alpha Blockade Index, or both. Further, standardizing may comprise mapping the possible range of scores for each the instrument to a range of conditional probabilities ranging from about 0 to about 1. Also, the standardizing may further comprise mapping each indeterminate score, if any, obtained from the instruments to a conditional probability of about 0.5. The range of possible scores of each the assessment instrument which constitutes an indeterminate score for the instrument may be defined such that the likelihood of diagnostic error for each the instrument does not exceed a certain preset probability. Additionally, the certain preset probability may be within the range of about 0.01 to about 0.1. Finally, the computational procedure may be, for example, one of the following: Sequential Bayesian inference procedure, computation of joint probability distribution, multiplication of probabilities, logical expression, or a combination thereof.

Example No. 3

Another aspect of an exemplary embodiment of the present invention is directed to a method, apparatus and/or computer program product for assessing individuals for disorders associated with attentional impairments, using scores obtained from two or more assessment instruments conducted on an individual. The related apparatus is a device configured to (a) calibrate the obtained scores by standardizing the range of obtainable scores for each of the instruments, and (b) perform a computation procedure upon the calibrated scores to produce a composite result. The assessment instruments may include, for example, two or more of the following: demographic questionnaires, behavioral checklists, psychometric tests, parent reports, teacher rating forms, or EEG-based vigilance, attention, and consistency measures. Also, the assessment instruments may include the Consistency Index, Alpha Blockade Index, or both. Further, standardizing may comprise mapping the possible range of scores for each the instrument to a range of conditional probabilities ranging from about 0 to about 1. Also, the standardizing may further comprise mapping each indeterminate score, if any, obtained from the instruments to a conditional probability of about 0.5. The range of possible scores of each the assessment instrument which constitutes an indeterminate score for the instrument may be defined such that the likelihood of diagnostic error for each the instrument does not exceed a certain preset probability. Additionally, the certain preset probability may be within the range of about 0.01 to about 0.1. Finally, the computational procedure may be, for example, one of the following: Sequential Bayesian inference procedure, computation of joint probability distribution, multiplication of probabilities, logical expression, or a combination thereof.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, section, abstract, drawing figure, etc.) of this application, unless clearly specified to the contrary, there is no requirement for any particular described or illustrated activity or element, any particular sequence of such activities, any particular size, speed, material, dimension, time period, or frequency, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive.

The invention may be embodied in other specific forms without departing from the spirit or essential characteristics thereof. The foregoing embodiments are therefore to be considered in all respects illustrative rather than limiting of the invention described herein.

REFERENCES

The following references, as cited throughout this document are hereby incorporated by reference in their entirety herein:

1. Ritchie, K., Artero, S., & Touchon, J., 2001. Classification criteria for mild cognitive impairment: A population based validation study. *Neurology* 56(1), 37-42.
2. Ballard, C, O'Brien, J. Gray, A., Cormack, F., Ayre, G., Rowan, E. H., Thompson, P., Bucks, R., McKeith, I., Walker, M., & Tovee, M., 2001. Attention and Fluctuating Attention in Patients with Dementia with Lewy Bodies and Alzheimer Disease. *Archives of Neurology,* 58(6), 977-982.
3. Grodstein, F., Chen, J., Wilson, R., & Manson, J., 2001. Type 2 Diabetes and Cognitive Function in Community Dwelling Elderly Women. *Diabetes Care,* 24(6), 1060-1065.
4. Sohlberg, M. & Mateer, C., 2001. Improving Attention and Managing Attentional Problems: Adapting Rehabilitation Techniques to Adults with ADD. *Annals of New York Academy of Sciences,* 931, 359-375.
5. Armstrong, C., Hayes, K, & Martin R., 2001. Neurocognitive Problems in Attention Deficit Disorder: Alternative Concepts and Evidence for Impairment in Inhibition of Selective Attention. *Annals of New York Academy of Sciences,* 931, 196-215.
6. Levin, H., Rossman, R., Rose, J., et al., 1979. Long-term neuropsychological outcome of closed head injury. *Journal of Neurosurgery,* 50, 412-422.
7. Meyer, J., Rauch, G., Rauch, R., Haque, A., & Crawford, K., 2000. Cardiovascular and Other Risk Factors for Alzheimer's Disease and Vascular Dementia. *Annals of New York Academy of Sciences,* 903, 411-423.
8. Chang, L, Speck, O., Miller, E., Braun, J., et al., 2001. Neural correlates of attention and working memory deficits in HIV patients. *Neurology,* 57(6), 1001-1007.
9. ADHD, NIH Consensus Statement, 1998. Diagnosis and Treatment of Attention Deficit Hyperactivity Disorder, November 16-18.
10. Pohjasvaara, T., Ylikoski, R., Leskela, M., et al., 2001. Evaluation of Various Methods of Assessing Symptoms of Cognitive Impairment and Dementia. *Alzheimer Disease and Associated Disorders,* 15(4), 184-193.
11. Lezak, M., Neuropsychological Assessment, Second Edition. New York: Oxford University Press, 1995.
12. Rosen, W., Mohs, R., & Davis, K., 1984. A new rating scale for Alzheimer's disease. *American Journal of Pschiatry,* 141, 1356-1364.
13. Doraiswamy, P., Kaiser, L., Bieber, F., & Garman, R., 2001. The Alzheimer's Disease Assessment Scale: Evaluation of Psychometric Properties and Patterns of Cognitive Decline in Multicenter Clinical Trials of Mild to Moderate Alzheimer's Disease. *Alzheimer Disease and Associated Disorders,* 15(4), 174-183.
14. MacArthur, J., Hoover, D., Bacellar, H., et al., 1993. Dementia in AIDS patients: incidence and risk factors. *Neurology,* 42, 2245-2252.
15. MacArthur, J., Cohen, B., Slenes, O., et al., 1989. Low prevalence of neurological and neuropsychological abnornmalities in other wise healthy HIV-1 infected individuals: Results from the Multicenter AIDS Cohort Study. *Annals of Neurology,* 26, 601-611.
16. Heaton, R., Grant, I., Butters, N., et al., 1995. The HNRC Neuropsychology of HIV infection at different stages. HIV Neurobehavioral Research Center. *Journal of International Neuropsychology Society,* 58, 231-251.
17. American Psychiatric Association, 1994. *Diagnostic and statistical manual of mental disorders* (4th ed.). Washington, DC: American Psychiatric Association.
18. Goldman, L. S., Genel, M., Bezman, R. J., and Slanetz, P. J. (1998). Council report of diagnosis and treatment of Attention-Deficit Hyperactivity Disorder in children and adolescents. *Journal of the American Medical Association,* 279, 1100-1107.
19. Cox D. J., Kovatchev B. P., Morris J. B., Jr., Phillips C., Hill R. J., Merkel L., "Electroencephalographic and Psychometric Differences Between Boys with and without Attention-deficit/Hyperactivity Disorder (ADHD): a pilot study," Appl. Psychophysiol Biofeedback 23:179-188, 1998.
20. DuPaul G. J., Power T. J., Anastopoulos A. D., Reid R., "Manual for the AD/RD." Rating Scale-IV. New York: Guildford Press, 1998.
21. Barkley, R. A., Guevremont, D. C., Anastopoulos A. D., DuPaul G. J., & Shelton T. L., 1993. Driving-related risks and outcomes of attention deficit hyperactivity disorder in adolescents and young adults: a 3- to 5-year follow-up survey. *Pediatrics,* 92, 212-218.

We claim:

1. A method of assessing an individual for disorders associated with attentional impairments, said method comprising:
    a) obtaining scores of two or more assessment instruments for attentional impairment, conducted on the individual, wherein the scores are representative of disorders of attentional impairments in the individual;
    b) standardizing, with a processor, the scores for each of said instruments, wherein said standardizing comprises mapping the possible range of scores for each said instrument to a range of conditional probabilities ranging from about 0 to about 1; and c) operating, with a processor, upon said standardized scores using a computational procedure to transform the standardized scores into a composite result that has a diagnostic error lower than any of the individual assessment instruments alone.

2. The method of claim 1, wherein said assessment instruments include two or more of the following: demographic questionnaires, behavioral checklists, psychometric tests, parent reports, teacher rating forms, or EEG-based vigilance, attention, and consistency measures.

3. The method of claim 2, wherein said assessment instruments include the Consistency Index, Alpha Blockade Index, or both.

4. The method of claim 1, wherein said standardizing further comprises mapping each indeterminate score, if any, obtained from said instruments to a conditional probability of about 0.5.

5. The method of claim 4, wherein the range of possible scores of each said assessment instrument which constitutes an indeterminate score for said instrument is defined such that the likelihood of diagnostic error for each said instrument does not exceed a certain preset probability.

6. The method of claim 5, wherein said certain preset probability is within a range of about 0.01 to about 0.1.

7. The method of claim 1, wherein said computational procedure is one of the following:

Sequential Bayesian inference procedure, computation of joint probability distribution, multiplication of probabilities, logical expression, or a combination thereof.

8. A computer program product embodied on computer-readable media for assessing an individual for disorders associated with attentional impairments, programmed to perform the following:

a) obtaining scores of two or more assessment instruments for attentional impairment, conducted on the individual, wherein the scores are representative of disorders of attentional impairments in the individual;

b) standardizing the scores for each of said instruments, wherein said standardizing comprises mapping the possible range of scores for each said instrument to a range of conditional probabilities ranging from about 0 to about 1;

c) operating upon said standardized scores using a computational procedure to transform the standardized scores into a composite result that has a diagnostic error lower than any of the individual assessment instruments.

9. The computer program product of claim 8, wherein said assessment instruments include two or more of the following: demographic questionnaires, behavioral checklists, psychometric tests, parent reports, teacher rating forms, or EEG-based vigilance, attention, and consistency measures.

10. The computer program product of claim 9, wherein said assessment instruments include the Consistency Index, Alpha Blockade Index, or both.

11. The computer program product of claim 8, wherein said standardizing further comprises mapping each indeterminate score, if any, obtained from said instruments to a conditional probability of about 0.5.

12. The computer program product of claim 11, wherein the range of possible scores of each said assessment instrument which constitutes an indeterminate score for said instrument is defined such that the likelihood of diagnostic error for each said instrument does not exceed a certain preset probability.

13. The computer program product of claim 12, wherein said certain preset probability is within a range of about 0.01 to about 0.1.

14. The computer program product of claim 8, wherein said computational procedure is one of the following: Sequential Bayesian inference procedure, computation of joint probability distribution, multiplication of probabilities, logical expression, or a combination thereof.

15. A method of diagnosing an attentional impairment disorder comprising:

standardizing, with a processor, scores from a plurality of attentional impairment assessment instruments by translating each score into a conditional probability for a particular attentional impairment to produce a standardized result for each score respectively; and performing, with a processor, a computational procedure on the standardized results to transform the standardized results into a combined result, wherein the combined result is more accurate than each of the standardized results alone.

16. The method of claim 15, wherein said assessment instruments include two or more of the following:

demographic questionnaires, behavioral checklists, psychometric tests, parent reports, teacher rating forms, or EEG-based vigilance, attention, and consistency measures.

17. The method of claim 16, wherein said assessment instruments include the Consistency Index, Alpha Blockade Index, or both.

18. The method of claim 15, wherein said standardizing comprises mapping the possible range of scores for each said instrument to a range of conditional probabilities ranging from about 0 to about 1.

19. The method of claim 18, wherein said standardizing further comprises mapping each indeterminate score, if any, obtained from said instruments to a conditional probability of about 0.5.

20. The method of claim 19, wherein the range of possible scores of each said assessment instrument which constitutes an indeterminate score for said instrument is defined such that the likelihood of diagnostic error for each said instrument does not exceed a certain preset probability.

21. The method of claim 20, wherein said certain preset probability is within a range of about 0.01 to about 0.1.

22. The method of claim 15, wherein said computational procedure is one of the following: Sequential Bayesian inference procedure, computation of joint probability distribution, multiplication of probabilities, logical expression, or a combination thereof.

23. A computer program product embodied on computer-readable media for diagnosing an attentional impairment disorder comprising:

standardizing scores of a plurality of attentional impairment assessment instruments by translating each score into a conditional probability for a particular attentional impairment to produce a standardized result for each score respectively; and performing a computational procedure on the standardized results to transform the standardized results into a combined result, wherein the combined result is more accurate than each of the standardized results alone.

24. The computer program product of claim 23, wherein said assessment instruments include two or more of the following: demographic questionnaires, behavioral checklists, psychometric tests, parent reports, teacher rating forms, or EEG-based vigilance, attention, and consistency measures.

25. The computer program product of claim 24, wherein said assessment instruments include the Consistency Index, Alpha Blockade Index, or both.

26. The computer program product of claim 23, wherein said standardizing comprises mapping the possible range of scores for each said instrument to a range of conditional probabilities ranging from about 0 to about 1.

27. The computer program product of claim 26, wherein said standardizing further comprises mapping each indeterminate score, if any, obtained from said instruments to a conditional probability of about 0.5.

28. The computer program product of claim 27, wherein the range of possible scores of each said assessment instrument which constitutes an indeterminate score for said instrument is defined such that the likelihood of diagnostic error for each said instrument does not exceed a certain preset probability.

29. The computer program product of claim 28, wherein said certain preset probability is within a range of about 0.01 to about 0.1.

30. The computer program product of claim 23, wherein said computational procedure is one of the following: Sequential Bayesian inference procedure, computation of joint probability distribution, multiplication of probabilities, logical expression, or a combination thereof.

* * * * *